United States Patent [19]

Patzke et al.

[11] Patent Number: 5,447,070
[45] Date of Patent: Sep. 5, 1995

[54] ROTOR OF AN ULTRASONIC TEST DEVICE FOR DETECTION OF OBLIQUE DEFLECTS

[75] Inventors: Ottokar Patzke, Erftstadt-Lieblar; Reinhard Prause, St. Agustin; Rudolf Mietzner, Hurth, all of Germany

[73] Assignee: Krautkramer GmbH & Co., Germany

[21] Appl. No.: 50,344

[22] PCT Filed: Oct. 28, 1991

[86] PCT No.: PCT/DE91/00839
§ 371 Date: May 12, 1993
§ 102(e) Date: May 12, 1993

[87] PCT Pub. No.: WO92/08970
PCT Pub. Date: May 29, 1992

[30] Foreign Application Priority Data

Nov. 12, 1990 [DE] Germany ............. 40 36 005.9

[51] Int. Cl.6 ............................................. G01N 29/26
[52] U.S. Cl. .............................. 73/621; 73/622; 73/624; 73/634
[58] Field of Search ............... 73/621, 622, 624, 628, 73/633, 634, 625

[56] References Cited

U.S. PATENT DOCUMENTS

| | | | |
|---|---|---|---|
| 3,958,451 | 5/1976 | Richardson | 73/622 |
| 4,395,911 | 8/1983 | Macecek | 73/622 |
| 5,280,724 | 1/1994 | Higo et al. | 73/624 |

FOREIGN PATENT DOCUMENTS 9010086 10/1990 Germany .

Primary Examiner—Hezron E. Williams
Assistant Examiner—Rose M. Finley
Attorney, Agent, or Firm—Eckert Seamans Cherin & Mellott

[57] ABSTRACT

A rotor of on ultrasonic testing device for rotation-symmetrical test-pieces has drillings arranged in pairs for test head supports and test head supports arranged in these drillings. These supports are longitudinally adjustable along the axis of the drilling. The supports are sealed in the drilling and carry at least one test head. The drillings arranged in pairs are arranged in staggered array along the axis of rotation of the rotor or around the periphery of the rotor. Each pair has a rotary drive which as a shared activating system and facilitates synchronous rotation in an opposite direction of the two test head supports of the pair around the axis of the drilling.

12 Claims, 3 Drawing Sheets

ROTOR OF AN ULTRASONIC TEST DEVICE FOR DETECTION OF OBLIQUE DEFLECTS

The invention pertains to a rotor of an ultrasonic test device for rotationally symmetrical test pieces, especially tubes and bars. The rotor has at least one bore for a test probe mount. The bore holds a test probe mount, which a) can be longitudinally adjusted in the direction of the axis of the bore, b) is sealed in the bore by a gasket, and c) holds at least one test probe. In this rotor, which is anticipated in DE-U-901 0066, the test probe mounts can be angularly adjusted, thereby making it possible to detect oblique defects lying within a given angular range.

In practical situations, it was then found that oblique defects frequently occur in such a way that they are present in a positive angular range, measured relative to the axis of the test piece, and in a numerically equal, but negative angular range. The detection of these kinds of oblique defects with the previously known rotor is difficult.

The goal of the invention was to further develop the previously known rotor of the type described at the beginning in such a way that it would be possible to determine not only the types of defects that can already be detected with existing equipment, but also to simplify the detection of oblique defects that occur both in a positive angular range (measured relative to the axis of the test piece) and in a numerically equal, but negative angular range.

The oblique defects can be systematically detected in a positive angular range (relative to the axis of the test piece) by the first test probe mount of the pair, and the oblique defects in the numerically equal, but negative angular range can be detected by the second test probe mount. By adjusting the interplay of the two test probe mounts from the outside, it is possible to detect oblique defects of a desired orientation. In this connection, the equipment of the invention can be quickly adapted to the specific test objective.

The goal of the invention was to further develop the previously known rotor of the type described at the beginning in such a way that it would be possible to determine not only the types of defects that can already be detected with existing equipment, but also to perform oblique error testing in ultrasonic rotational test systems.

In accordance with the invention, starting with the rotor of the type described at the beginning, this goal is achieved by providing pairs of bores, which are arranged in staggered fashion in the direction of the axis of rotation of the rotor, and that a rotational drive is assigned to each test probe mount of a pair, which rotational drive has a common control and allows synchronous, opposing rotation of the two test probe mounts of the pair about the given axis of the bore.

In accordance with the invention, it is possible systematically to determine oblique defects that lie within a given angular range. In this connection, a minimum of one test probe of the first test probe mount of a pair is set to determine oblique defects of a first angular range, while a minimum of one test probe of the second test probe mount of the pair detects oblique defects of another angular position. Especially advantageous in this regard is a design in which the oblique defect is detected by the first test probe mount of the pair in a positive angular range (relative to the axis of the test piece), and the oblique defect is detected by the second test probe mount in the negative angular range of the same magnitude. By adjusting the interplay of the two test probe mounts from the outside, it is possible to detect oblique defects of a desired orientation. In this connection, the equipment of the invention can be quickly adapted to the specific test objective.

Oblique defects arise, for example, in the production of tubes or bars by the continuous casting or continuous drawing process, if the production process also involves rotation (torsion). The generally areal defects may also by variably inclined to their given angular position relative to the axis of the test piece. To assure reliable detection, it is proposed, in a further modification, that each test probe mount have two identically designed test probes, whose central test beams lie in a plane, which preferably runs through the central axis of the two bores of the pair of test probe mounts.

In this connection, it is especially advantageous if the central test beams of the test probes of a pair intersect at a point located a few centimeters from the test probes. In the practical performance of the test, this point of intersection is adjusted in such a way that it lies on or near the vertical line of a test piece. In this way, when the two test probe mounts of a pair are rotated, the geometry undergoes practically no change during the ultrasonic irradiation, which is a great advantage.

Furthermore, it was found to be advantageous to arrange a given pair of test probe mounts in a cylindrical test probe holder, which has the two bores for the test probe mounts and in turn is mounted in a mounting bore of the rotor, holds the rotational drive, including the control, and is sealed in the mounting bore in such a way that it can be moved in the longitudinal direction. In this way, the two test probe holders of a pair can be adjusted together in the longitudinal direction of the bores; this also simplifies the design and operation of the equipment.

It is also possible to have more than two, preferably identically designed, test probes per test probe mount. An even number of test probes is advantageous. They are preferably uniformly distributed on a circular arc.

Other advantages and features of the invention are specified in the secondary claims and in the following description of a specific embodiment of the invention, which is explained with reference to the drawings. It is understood that the invention is by no means limited to this specific example.

Figure 1:
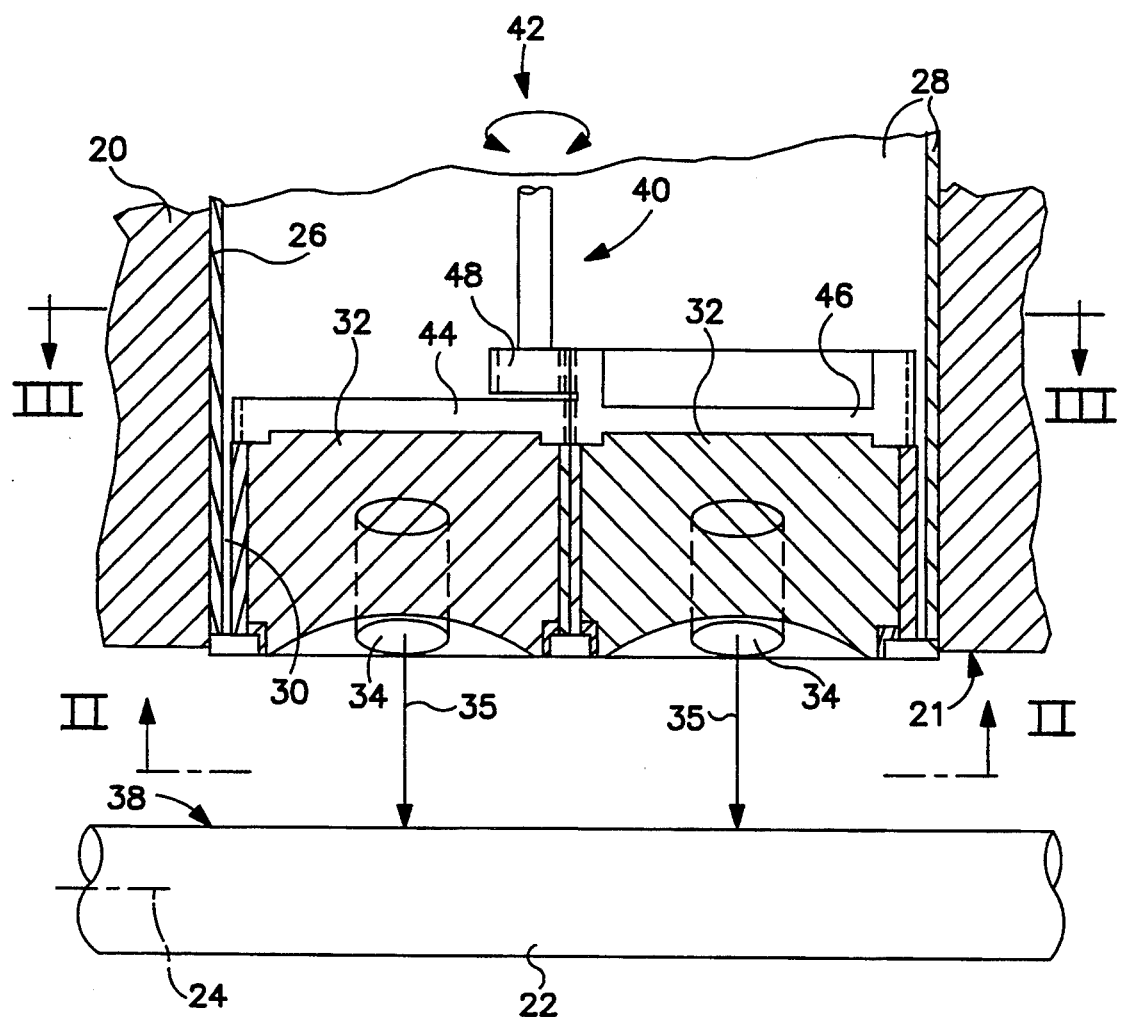
FIG. 1 shows an axial section (schematic) through a rotor with a pair of test probe mounts, each of which has two test probes.

This specific embodiment, especially FIG. 1, shows a section of a rotor 20, which can be rotated around a test piece 22, which passes through its main bore 21. The axis 24 of this test piece coincides with the axis of rotation of the rotor 20. A radial mounting bore 26 is formed in the rotor 20. It passes through the rotor and thus extends from the outer surface of the rotor to its inner surface. A mount 28 is inserted in the bore. It can be moved in the direction of the axis of the mounting bore 26 by means of an adjusting device (not shown, since it is state of the art).

The mount 28 has two bores 30 positioned an equal distance from the axis of the mounting bore 26 and parallel to it. The centers of the two bores 30 are displaced in the direction of the axis 24 of the test piece and lie as close as possible to each other. The center axis of these two bores 30 coincides with the axis of the mounting bore 26. Each bore 30 contains a test probe mount 32; the two test probe mounts 32 form a pair and are identical in design. Each test probe mount 32 has two test probes 34, which are also identical in design. They are arranged on a circular arc around the axis of the bore 30, displaced from each other by 180° and directed towards the test piece 22. They are mounted obliquely in the test probe mount 32, with the result that their central test beams 35 intersect at intersection point 36. In other words, the central test beams 35 of the two test probes 34 of a test probe mount 32 form a V-shaped configuration. The point of intersection 36 is located on the top 38 of the cylindrical test piece 22, regardless of the rotational orientation of the two test probes 34 of each test probe mount 32.

The two test probe mounts 32 of a pair are rotationally connected. This is accomplished by means of a rotational drive 40, which acts on both test probe mounts 32 and has a control 42, which is accessible on the outer cylindrical surface of the rotor 20 and is designed, for example, as a polyhedron.

The rotational drive 40 can be designed in any desired way, as long as it satisfies the requirement that both test probe mounts 32 are rotationally connected with each other in such a way that the rotation of one test probe mount 32 through a certain angle causes rotation of the other test probe mount of the pair through the same angle. However, the two test probe mounts of a pair rotate in opposite directions.

In the concrete example shown here, a radially toothed gear 44, 46 is provided on the radially outer end of each test probe mount 32. Its diameter corresponds to the diameter of the bore 30. The two gears 44, 46 are engaged with each other and are angularly displaced relative to each other by half a tooth space. They produce rotational connection of the two test probes 34 of the pair. The gear 46 of the test probe mount 32 on the right in FIG. 1 has a greater axial length and at the same time is used for the drive. For this purpose, a drive gear 48, which is also radially toothed, engages the upper area of the gear 46; the drive gear 48 is connected with the control 42 of the rotational drive 40 via a reduction gear, which is not shown in detail here. A scale is also provided here, on which the present rotational position of the test probes 34 or the test probe mounts 32 can be read. These things are part of the present state of the art and therefore are not shown in detail.

Figure 2:
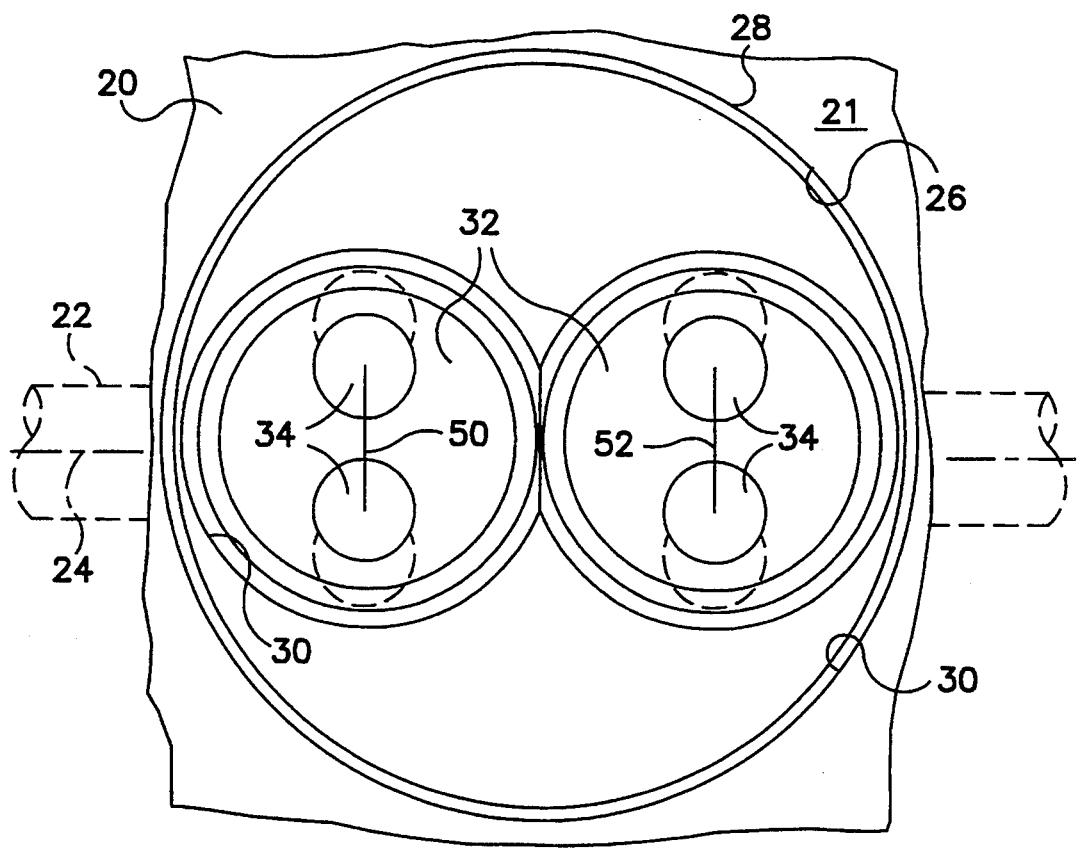
FIG. 2 is a view along line II—II in FIG. 1.

FIG. 2 shows a view radially outward towards the two test probe mounts 32 and the rotor 20. The connecting line 50, 52 of the two test probes 34 of the two test probe mounts 32 runs at an angle of ca. 90° to the axis of rotation of the rotor 20. During practical operation, the two test probe mounts 32 are adjusted in such a way that the angular position has the same absolute value and differs only in sign. This has the effect that one of the test probe mounts detects oblique defects in the positive angular position, while the other test probe mount detects corresponding defects in the negative angular position.

Figure 3:
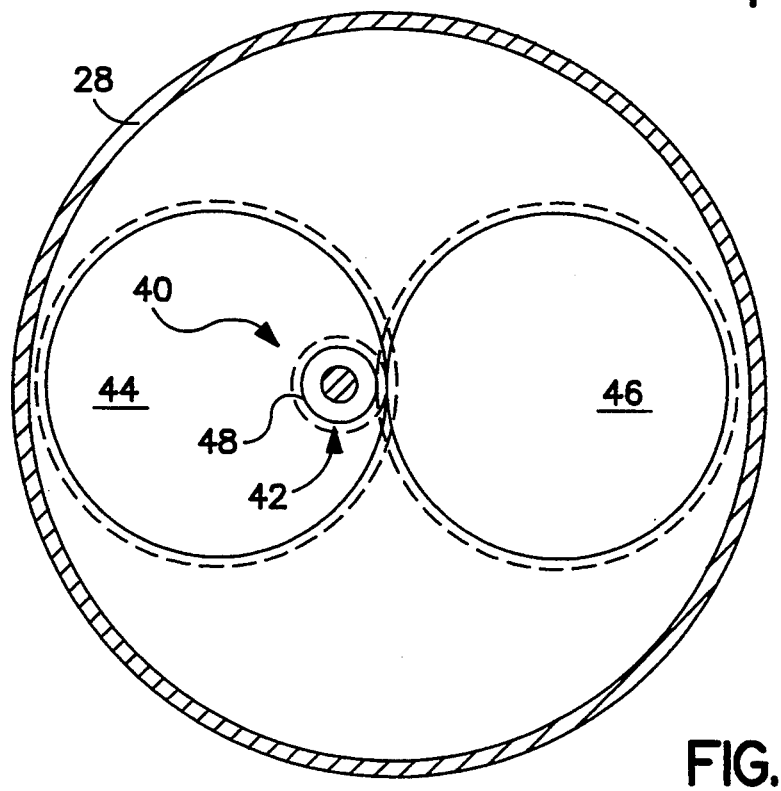
FIG. 3 is a cross section in the region of line III—III in FIG. 1.

FIG. 3 shows the rotational drive 40. The two gears 44, 46 are essentially the same in design, except for their different radial dimensions. The drive gear 48 is engaged with the right gear 46 and in turn is rotationally connected with a rod that is part of the control 42.

If the two test probes 34 of each test probe mount 32 are aligned in such a way that their connecting line 50, 52 runs perpendicularly to the axis 24 of the test piece, longitudinal defects can be detected. This corresponds to the representation shown in FIG. 1. On the other hand, if the two test probes 34 of each test probe mount 32 are aligned in such a way that their connecting line 50, 52 runs parallel to the axis 24 of the test piece, transverse defects can be detected. In the intermediate angular range above 0° and below 90°, in which the two test probe mounts 32 can be fixed in any desired position, oblique defects of the corresponding orientation are detected.

When a 180° rotation of the two test probe mounts 32 is performed, the same state is obtained as before from a measuring technology standpoint.

Figure 4:
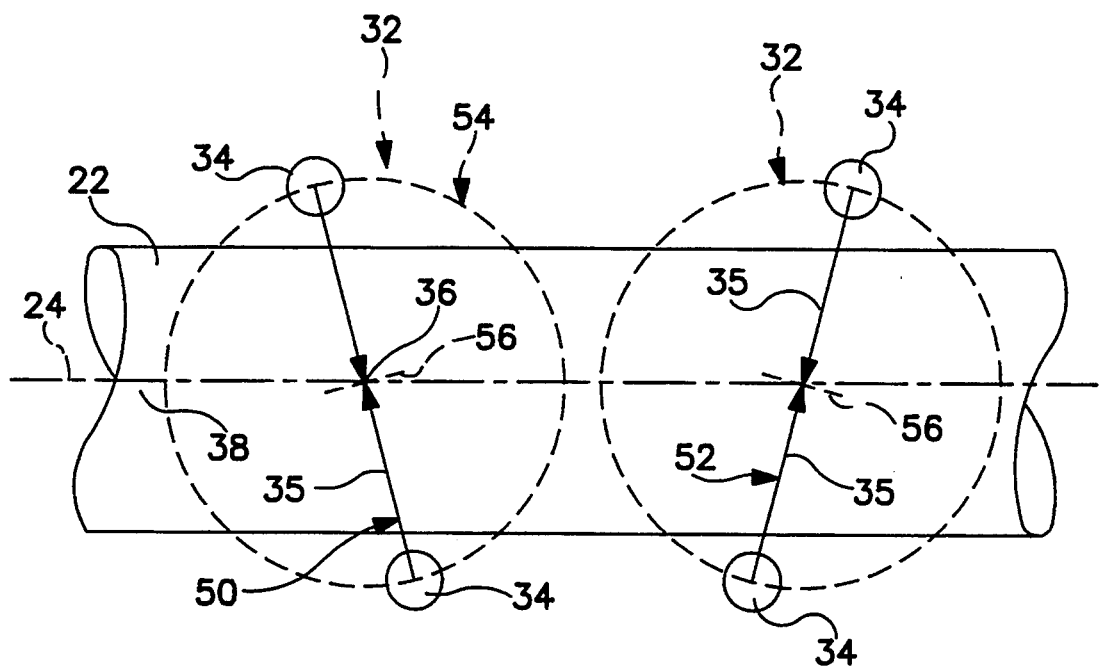
FIG. 4 is a schematic representation for illustrating the process sequence. The drawing shows a cylindrical test piece, above which there are two test probe mounts, each of which has two test probes displaced from each other by 180 degrees.
Figure 5:
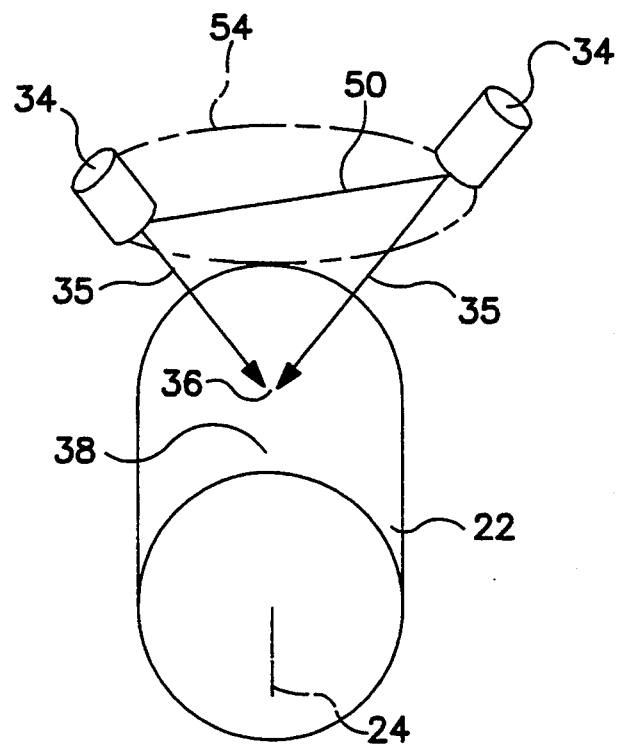
FIG. 5 is a perspective front view of a system as shown in FIG. 4, but the drawing shows only two test probes of a test probe mount, which is otherwise not shown in detail.

The measuring process will now be explained with reference to the schematic drawings in FIGS. 4 and 5. FIG. 4 shows a top view, and FIG. 5 shows a corresponding front perspective view. Above the cylindrical test piece 22, there are two (or only one in FIG. 5) test probe mounts 32, which are only indicated by their respective test probes 34 and their circle of movement 54. The test probes 34 of each test probe mount are aligned in such a way that their central test beams 35 run together in a V-shaped configuration to a point of intersection 36, which in the representation shown here is located perpendicularly below the center of the circle of movement 54 of the two test probes 34. This point of intersection lies on the top 38 of the cylindrical test piece 22. Directly below it there is an oblique defect 56. For the left pair of test probes 34, it runs at an angle of plus 15° to the axis 24 of the test piece, and for the two test probes 34 of the other test probe mount 32 of the pair (on the right in FIG. 4), it runs at an angle of minus 15° to the axis 24 of the test piece. The connecting line 50 or 52 of the two test probes 34 runs at right angles to it. In this way, the central test beams 35 hit the oblique defect 56 transversely to its longitudinal dimension. Since the test probes 34 apply the ultrasonic radiation obliquely, they can preferentially detect oblique defects 56 that are inclined in the radial direction. In this way, each of the two test probes 34 of a test probe mount preferentially detects a different inclination orientation of oblique defects 56.

We claim:

1. A rotor of an ultrasonic test device for rotationally symmetrical test pieces wherein:
   the rotor has a cylindrical outer surface and is formed with a main bore having an axis of rotation,
   a mounting fixture coupled to the rotor, the mounting fixture being formed with at least one pair of closely neighboring test probe mount bores, wherein the test probe mount bores are staggered relative to each other with respect to the axis of rotation, each of the test probe mount bores having a test probe mount axis lying in a plane perpendicular to the axis of rotation,
   at least one pair of test probe mounts, the pair of test probe mounts having a first and second test probe mount, each test probe mount being engaged in one of the pair of test probe mount bores, each test probe mount being sealed in the test probe mount bore by a gasket and being longitudinally adjustable along the test probe mount axis, a least one test probe engaged in each said test probe mount, a rotational drive coupled to the at least one pair of test probe mounts, the rotational drive having a common control that is accessible on the outer cylindrical surface of the rotor, the rotational drive providing synchronous, opposing rotation of the pair of test probe mounts in the test probe mount bore, each test probe mount rotating about the test probe mount axis, whereby oblique defects in a positive angular range relative to the axis of rotation can be detected by the first test probe mount of the pair, and oblique defects in a numerically equal negative angular range can be detected by the second test probe mount of the pair.

2. The rotor of claim 1, wherein each test probe mount of the pair holds two identically designed test probes, each test probe having a central test beam, the central test beams of the two test probes lying in a plane, which runs through the test probe mount axis.

3. The rotor of claim 1, further comprising:

a mounting bore formed in the rotor, the mounting bore having a mounting bore axis perpendicular to the axis of rotation, the mounting bore extending from the cylindrical outer surface to the main bore of the rotor, said mounting fixture being cylindrical in shape and engaged in the mounting bore, the mounting fixture being formed with the at least one pair of test probe mount bores and containing the rotational drive and the common control, the mounting fixture being engaged in the mounting bore such that it can be moved in the longitudinal direction along the mounting bore axis.

4. The rotor of claim 2, wherein the test piece has a surface and the central test beams of the test probes intersect in a point of intersection, which is located on the surface of the test piece.

5. The rotor of claim 1, wherein an even number of test probes are uniformly circularly distributed in each test probe mount.

6. The rotor of claim 1, wherein at least two pairs of test probe mounts are arranged at an equal spacing angle.

7. The rotor of claim 2, wherein the test piece has an axis which is coincident to the axis of rotation and the central test beams run perpendicularly to the test piece axis in a selected rotational position of the two test probe mounts of the pair.

8. The rotor of claim 1, wherein each of the test probes of the pair of test probes, when set at an identical absolute angle, are located at an identical distance from a test piece.

9. The rotor of claim 1, wherein each of the test probes of a test probe mount are oriented at an angle of 10° to 25°, relative to the test probe mount axis.

10. The rotor of claim 1, wherein the test probes are connected to each other by a device for adjusting an angle of inclination of the test probes, transverse to the test probe mount axis and the axis of rotation, such that it possible to adjust the test probes at an angle greater than 0° and less than 45°.

11. The rotor of claim 5, wherein four test probes are uniformly circularly distributed in each test probe mount.

12. The rotor of claim 10, wherein each of the test probes of the pair are oriented at an angle of 17°, relative to the test probe mount axis.

* * * * *